US00PP33082P2

(12) United States Plant Patent
Asanoma

(10) Patent No.: US PP33,082 P2
(45) Date of Patent: May 18, 2021

(54) ***AJUGA* PLANT NAMED 'ASAAJ3'**

(50) Latin Name: *Ajuga reptans*
Varietal Denomination: ASAAJ3

(71) Applicant: Asanoma Engei, Kitashitara-gun (JP)

(72) Inventor: Tatsuya Asanoma, Aichi-prefecture (JP)

(73) Assignee: Asanoma Engei, Kitashitara-Gun (JP)

( * ) Notice: Subject to any disclaimer, the term of this patent is extended or adjusted under 35 U.S.C. 154(b) by 0 days.

(21) Appl. No.: 16/873,434

(22) Filed: Apr. 10, 2020

(51) Int. Cl.
*A01H 6/00* (2018.01)
*A01H 5/02* (2018.01)

(52) U.S. Cl.
USPC ..... Plt./401

(58) Field of Classification Search
USPC ..... Plt./401
CPC ..... A01H 6/00; A01H 5/02; A01H 6/50
See application file for complete search history.

*Primary Examiner* — Keith O. Robinson
(74) *Attorney, Agent, or Firm* — Cassandra Bright

(57) ABSTRACT

A new and distinct cultivar of *Ajuga reptans* plant named 'ASAAJ3' is disclosed, characterized striking green and white variegated foliage with dark green edges and a lighter green pattern in the middle of the leaf. Plants are low growing and compact, having a groundcover habit. This is a low maintenance plant with violet blue flowers. The new variety is a *Ajuga*, plants are useful for a variety of ornamental purposes, including outdoor containers and landscape.

2 Drawing Sheets

Latin name of the genus and species: *Ajuga reptans.*
Variety denomination: 'ASAAJ3'.

BACKGROUND OF THE INVENTION

The new *Ajuga* cultivar is the product of chance discovery. The new variety was discovered as a naturally occurring whole plant mutation of the parent variety, *Ajuga reptans* 'White Variegata', unpatented.

The discovery was made in the inventor's garden in Aichi-prefecture, Japan, during Spring of 2015.

Asexual reproduction of the new cultivar 'ASAAJ3' was first performed in Aichi-prefecture, Japan by terminal vegetative cuttings in February of 2016. 'ASAAJ3' has since produced multiple generations and has shown that the unique features of this cultivar are stable and reproduced true to type.

SUMMARY OF THE INVENTION

The cultivar 'ASAAJ3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ASAAJ3' These characteristics in combination distinguish 'ASAAJ3' as a new and distinct *Ajuga reptans* cultivar:

1. Striking green and white variegated foliage. Dark green edges with a lighter green pattern in the middle of the leaf.
2. Compact, groundcover habit.
3. Violet-blue flowers.
4. Low maintenance plant.

PARENTAL COMPARISON

Plants of the new cultivar 'ASAAJ3' are similar to plants of the parent, in most horticultural characteristics, however, plants of the new cultivar 'ASAAJ3' differ in the following:

1. Foliage of the new variety has a larger green margin and a green pattern in the center of the leaf not found in the parent variety.
2. The new variety is a more vigorous plant and grows faster.

COMMERCIAL COMPARISON

Plants of the new cultivar 'ASAAJ3' are comparable to the known, unpatented, *Ajuga* 'Arctic Fox', unpatented. Plants are similar in most horticultural characteristics; however, the new variety 'ASAAJ3' differs in the following:

1. Foliage of the new variety is larger (about 6-8 cm long), compared to the smaller foliage of 'Arctic Fox'(2 to 4 cm long).
2. The new variety propagates easier and faster than 'Arctic Fox'.

BRIEF DESCRIPTION OF THE PHOTOGRAPHS

Figure 1:
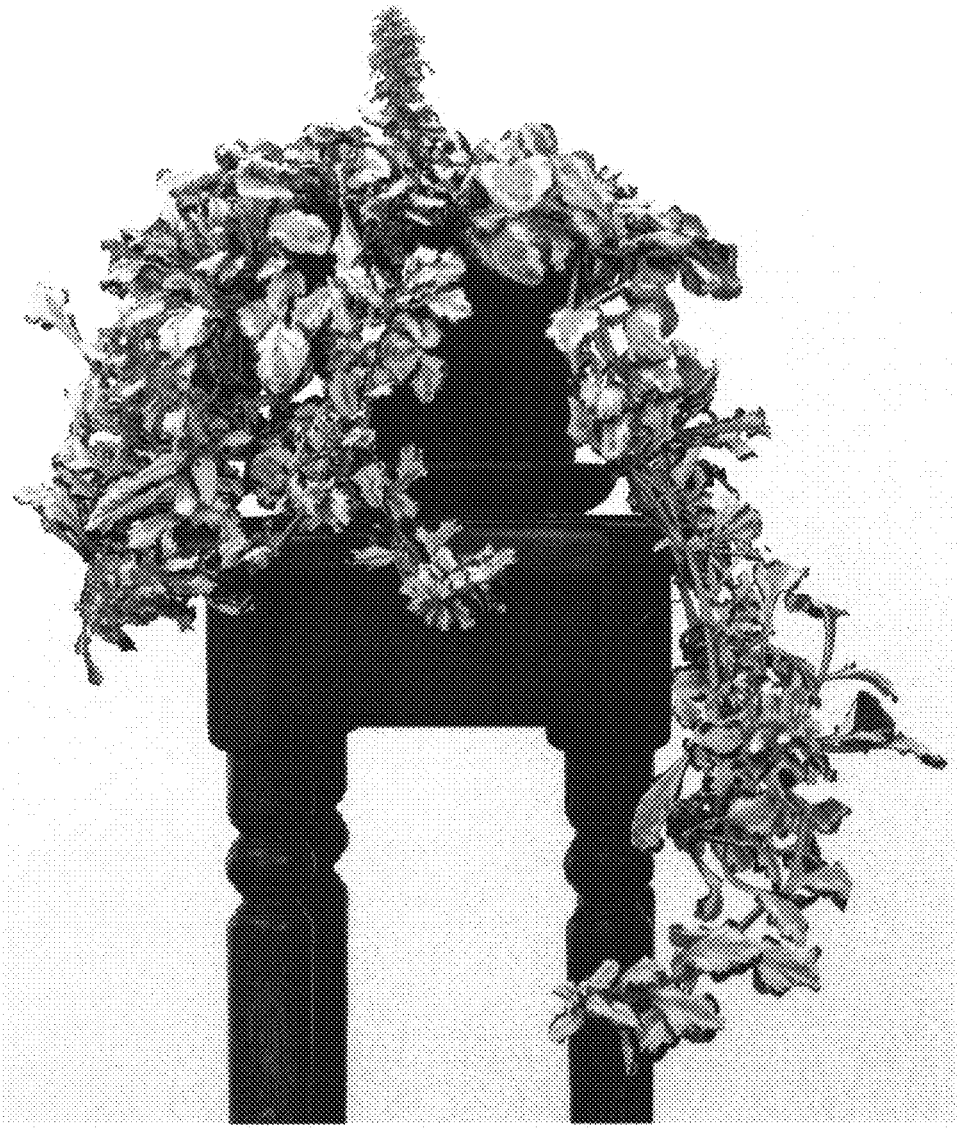

The accompanying photograph in FIG. 1 illustrates in full color a typical plant of 'ASAAJ3' grown outdoors in Boskoop, NL. Age of the plant is approximately 18 months.

Figure 2:
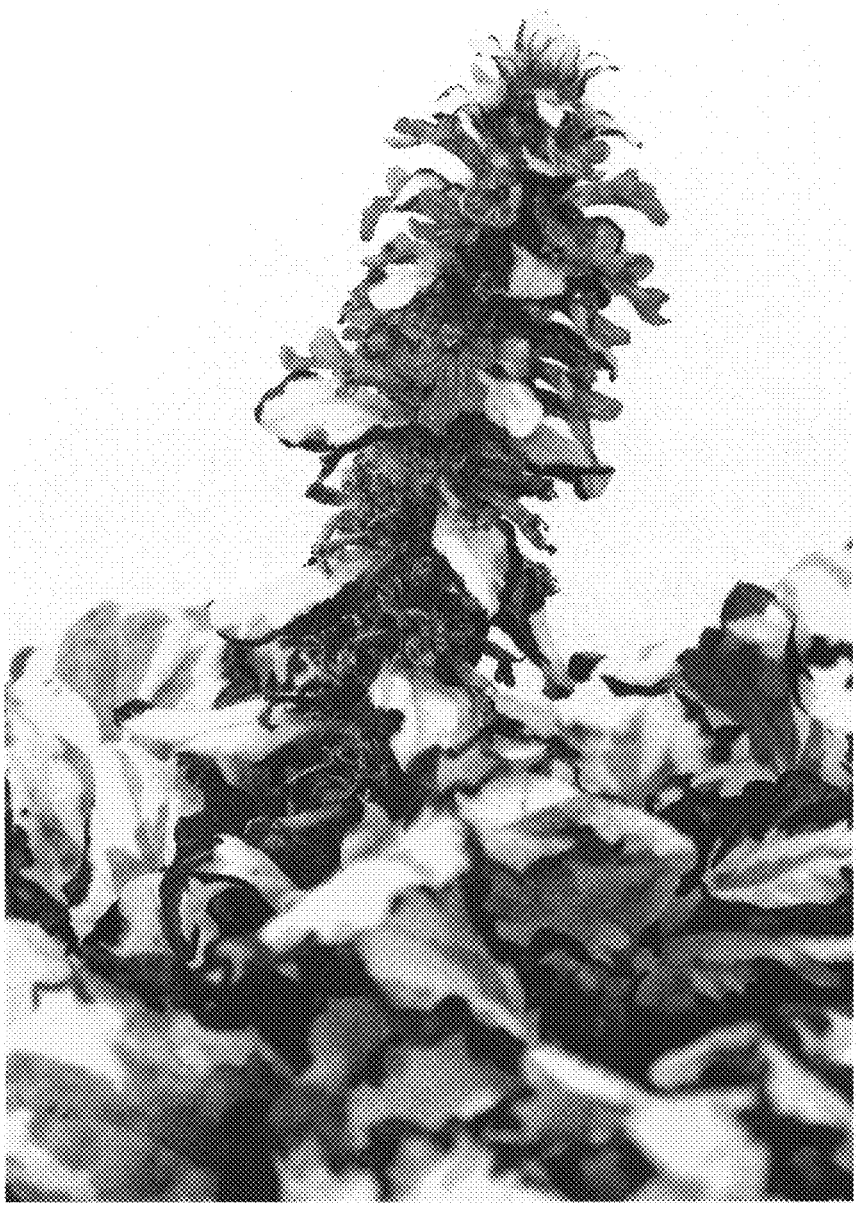

FIG. 2 illustrates a close-up view of the foliage and flowers.

The photographs were taken using conventional techniques and although colors may appear different from actual colors due to light reflectance it is as accurate as possible by conventional photographic techniques. No artificial light, photoperiodic treatments or chemical treatments were given to the plants.

DETAILED BOTANICAL DESCRIPTION

In the following description, color references are made to The Royal Horticultural Society Colour Chart, 2015 except where general terms of ordinary dictionary significance are used. The following observations and measurements describe 'ASAAJ3' plants grown outdoors in Boskoop, NL. Temperatures ranged from approximately 18° C. to 30° C. during the day and approximately 8° C. to 20° C. at night. No artificial light, photoperiodic treatments or chemical treatments were given to the plants. Measurements and numerical values represent averages of typical plant types. Botanical classification: *Ajuga reptans* 'ASAAJ3'.

PROPAGATION

Type of propagation typically used: Terminal vegetative cuttings.

Time to initiate roots: About 25 days at approximately 20° C.

Root description: Fibrous, brown, not accurately measured with a color chart.

PLANT

Age of plant described: Approximately 12 months.

Container size of the plant described: 13 cm.

Growth habit: Herbaceous perennial, trailing habit.

Height: Approximately 9 cm to top of highest leaf. Approximately 14.8 cm to top of highest inflorescence.

Plant spread: 60.5 cm.

Growth rate: Moderate to rapid.

Branching characteristics: Free branching, lateral branches. Pinching is not required, but increases branching.

Length of primary lateral branches: Average 21.6 cm.

Diameter of lateral branches: 3.5 mm.

Quantity of primary lateral branches: About 40. Secondary branches: Average 2 per branch.

Characteristics of primary lateral branches:

- *Form*.—Quadrangular.
- *Color*.—Developing: Near RHS Purple N77B. Mature: Near RHS Yellow-Green 144B. At Nodes: Near RHS Yellow-Green 144A.
- *Texture*.—Glabrous.
- *Strength*.—Strong.
- *Appearance*.—Glossy.
- *Aspect*.—Main stems in an average angle of 80°.

Internode Length: Average 3.9 cm.

FOLIAGE

Leaf:

- *Arrangement*.—Opposite, single.
- *Quantity*.—24 (12 pairs) per branch.
- *Average length*.—Approximately 6 to 8 cm.
- *Average width*.—Approximately 3.8 cm.
- *Shape of blade*.—Spatulate.
- *Apex*.—Obtuse.
- *Base*.—Narrow cuneate.
- *Margin*.—Irregular angulate, strongly undulate.
- *Texture of top surface*.—Glabrous to very sparely pubescent.
- *Texture of bottom surface*.—Glabrous.
- *Appearance of top surface*.—Matte.
- *Appearance of bottom surface*.—Matte.

Color:

- *Young foliage upper side*.—Near Yellow-green 150D, irregularly margined green; 139A and slightly darker, and with a yellow-green central blotch; 148C.
- *Young foliage, under side*.—Near Yellow-green 154D, irregularly margined green; NN137A and 139A, and with a yellow-green central blotch; 147C.
- *Mature foliage, upper side*.—Near Yellow-green, white and green-white; 150D, 155A and 157C, irregularly margined green; 137B and 139A, and with a greyed-green central blotch; 191B and 194A. Occasionally leaves without the greyed-green central blotch are developed. Very occasionally solid green leaves are formed colored Green N137A.
- *Mature foliage, under side*.—Near RHS Yellow-green, white and green-white; 154D and lighter and 157A, irregularly margined green to yellow-green; 137 and in between 138B and 147A, and with a greyed-green central blotch; 191A. Occasionally leaves without the greyed-green central blotch are developed. Very occasionally solid yellow-green leaves are formed; colored 146A.
- *Venation*.—Type: Pinnate. Venation color upper side: Near RHS Yellow-Green 147A. Venation color under side: Near RHS Yellow-Green 144B.
- *Petiole*.—Length: 5.7 mm. Width: 3 mm. Texture: Glabrous. Appearance: Moderately glossy. Color: Near RHS Yellow-green 145B, margined Green 139A upper and lower surfaces.

FLOWER

Natural flowering season: Late Spring to late Summer.

Inflorescence type: Raceme.

Inflorescence size:

- *Height*.—Approximately 7.1 cm.
- *Width*.—Approximately 4.6 cm.

Quantity of inflorescence per plant: Average 125.

Quantity of flowers per inflorescence: Average 50.

Individual flowers: Labiate, single.

- *Length*.—Approximately 14 mm.
- *Diameter*.—Approximately 9 mm.
- *Throat diameter*.—2 mm.
- *Tube length*.—8 mm.
- *Tube diameter*.—2 mm.
- *Longevity on plant*.—About 10 days.
- *Persistent or self-cleaning*.—Self-cleaning.
- *Fragrance*.—None.

Petals:

- *Arrangement*.—Labiate, 2 small upper petals, 2 lateral and 1 lower petal.
- *Quantity per flower*.—5.
- *Size*.—Length: Upper petals average: 0.1 cm (excl. tube). Lateral petals average: 0.4 cm (excl. tube). Lower petal average: 0.5 cm (excl. tube). Width: Upper petals average: 0.2 cm. Lateral petals average: 0.3 cm. Lower petal average: 0.6 cm.
- *Margin*.—Entire.
- *Shape*.—Lanceolate.

Apex: Upper petals and lateral petals obtuse. Lower petal cleft into two lobes, tips of lobes obtuse.

- *Base*.—Fused.
- *Petal texture*.—Glabrous upper surfaces, lower surfaces moderately pubescent.
- *Petal appearance*.—Matte all surfaces.
- *Throat texture*.—Glabrous.
- *Tube texture*.—Upper (inner) side smooth and glabrous. Under (out) side moderately to densely pubescent with very short hairs, average length of hairs:

0.1 cm, colored White N155D. Petal Color: When opening: Petal color, upper surface: Upper petals near Violet-Blue; 97C and 97D, veined darker; 97A. Lateral petals Violet-Blue; 97B, veined darker; 95A and 95B. Lower petal Violet-Blue; 92B, veined darker; 95A and 95B. Petal color, under surface: All petals near Violet-Blue; 97B to 97C, slightly tinged Yellow-Green 148D. Petal Color, Fully opened: Upper surface: Upper petals Violet-Blue 97C. Veins 97A. Lateral petals and lower petal Violet-Blue; 96C and 96D. Veins 95B. Under surface: Upper petals and lateral petals Violet-Blue 94D. No visible venation. Lower petal Violet-Blue 94C. No visible venation. Color Changes when Aging: No significant change. Throat color: Violet-Blue 97C. Tube color: Violet-Blue 98C, inner and outer surface. No visible venation. Bud: Shape: Narrow ovate. Length: Approximately 9 mm. Diameter: Approximately 3 mm. Color: Violet-blue; 98B, tinged yellow-green at the top; 148D, immature sepals green-white; 157A, margined green; 143C. Texture: Densely pubescent with short hairs, average length of hairs: 0.1 cm, colored white; NN155D. Calyx: Shape: Rotate tubular. Length: 5 mm. Diameter: 3 mm. Sepals: Arrangement: Rotate. Quantity: 5. Shape: Narrow deltoid. Tip: Acute. Base: Fused. Margin: Entire. Texture: Glabrous upper surface. Lower surface densely pubescent. Appearance: Matte all surfaces. Length of sepal: Approximately 4.5 mm. Width of sepal: Approximately 1 mm. Color upper surface: Near RHS Green-White 157A, Green 143C. Color lower surface: Near RHS Green-White 157A, Green 143C.

*Peduncle*.—Length: Average 6.2 cm. Width: Approximately 4 mm. Strength: Moderately strong. Aspect: Straight, average able 45° from peduncle. Texture: Densely pubescent. Color: Near RHS Yellow-green 145A.

*Pedicels*.—Length: Approximately 0.5 mm. Width: Approximately 0.75 mm. Aspect: Straight, average able 45° from peduncle. Strength: Moderately strong. Texture: Moderately pubescent. Color: Near RHS Green 133A.

REPRODUCTIVE ORGANS

Stamens: (Androecium).

*Number*.—Average 4.

*Filament length*.—Approximately 1 mm.

*Filament color*.—Near RHS Violet-Blue 97D.

*Anther length*.—0.5 mm.

*Anther color*.—Near RHS Black 202A.

*Anther shape*.—Dorsifixed, short oblong.

*Pollen color*.—Near RHS Yellow 8C.

*Pollen quantity*.—Moderate.

Pistil: (Gynoecium).

*Number*.—*Average* 5.

*Length*.—Approximately 10 mm.

*Style color*.—Near RHS Violet-Blue 97B.

*Style length*.—Approximately 9 mm.

*Stigma*.—Length: Approximately 0.5 mm. Shape: Cleft. Color: Near RHS Blue 108C. Ovary Color: Near RHS Yellow-Green 144A.

OTHER CHARACTERISTICS

Fruits and seeds: Not observed to date.

Temperature tolerance: Tolerates temperatures from approximately −29° C. to at least 40° C.

Disease/pest resistance: Neither resistance nor susceptibility to normal diseases and pests of *Ajuga* observed.

Drought tolerance: No drought resistance observed.

What is claimed is:

1. A new and distinct cultivar of *Ajuga* plant named 'ASAAJ3' as herein illustrated and described.

* * * * *